US009579029B2

(12) United States Patent
Liu et al.

(10) Patent No.: US 9,579,029 B2
(45) Date of Patent: Feb. 28, 2017

(54) HEART RATE DETECTION METHOD USED IN EARPHONE AND EARPHONE CAPABLE OF DETECTING HEART RATE

(71) Applicant: Goertek, Inc., Weifang, ShanDong Province (CN)

(72) Inventors: Song Liu, Weifang (CN); Bo Li, Weifang (CN); Na Li, Weifang (CN)

(73) Assignee: GOERTEK, INC., Weifang, Shandong Province (CN)

( * ) Notice: Subject to any disclaimer, the term of this patent is extended or adjusted under 35 U.S.C. 154(b) by 0 days.

(21) Appl. No.: 14/901,581

(22) PCT Filed: May 25, 2015

(86) PCT No.: PCT/CN2015/079680
§ 371 (c)(1),
(2) Date: Dec. 28, 2015

(87) PCT Pub. No.: WO2016/011843
PCT Pub. Date: Jan. 28, 2016

(65) Prior Publication Data
US 2016/0206222 A1     Jul. 21, 2016

(30) Foreign Application Priority Data

Jul. 24, 2014    (CN) .......................... 2014 1 0354577
Aug. 25, 2014   (CN) .......................... 2014 1 0422936

(51) Int. Cl.
*A61B 5/0245*     (2006.01)
*A61B 5/024*      (2006.01)
(Continued)

(52) U.S. Cl.
CPC .......... *A61B 5/02438* (2013.01); *A61B 5/024* (2013.01); *A61B 5/6803* (2013.01);
(Continued)

(58) Field of Classification Search
None
See application file for complete search history.

(56) References Cited

U.S. PATENT DOCUMENTS 4,751,931 A *  6/1988  Briller ................. A61B 5/0428
                                                       600/509
4,793,361 A * 12/1988  DuFault .............. A61B 5/0452
                                                       600/509
(Continued)

FOREIGN PATENT DOCUMENTS

CN            102215740            7/2014

OTHER PUBLICATIONS

PCT/CN2015/079680, Written Opinion of the International Searching Authority dated Aug. 17, 2015, 4 pages and English Translation, 4 pages.

*Primary Examiner* — Kennedy Schaetzle
(74) *Attorney, Agent, or Firm* — Boyle Fredrickson, S.C.

(57) ABSTRACT

The present invention discloses a heart rate detection method used in an earphone and an earphone capable of detecting heart rate. The method comprises: providing a cavity inside the earphone, and installing a microphone in the cavity; providing an acceleration sensor in the earphone; performing self-adaptive filtering process on signals collected by the acceleration sensor, and obtaining estimated signals of the signals generated by body movement of a wearer in the signals collected by the microphone; subtracting the estimated signals from the signals collected by the microphone to obtain signals related to heart rate; and detecting heart rate according to the signals related to heart rate. The technical scheme of the invention adopts an enclosed cavity to place the microphone to reduce interference of external noises and reinforce signal information collected by the microphone. By performing self-adaptive filtering on signals collected by the acceleration sensor to (Continued)

obtain estimated signals, subtracting the estimated signals from the signals collected by the microphone, and then detecting the heart rate, the influence of the body movement of the wearer on heart rate detection can be eliminated.

14 Claims, 6 Drawing Sheets

(51) Int. Cl.
  *H04R 1/10* (2006.01)
  *A61B 5/00* (2006.01)
  *G10L 21/0208* (2013.01)
  *H04R 29/00* (2006.01)
(52) U.S. Cl.
  CPC ............ *A61B 5/721* (2013.01); *A61B 5/7225* (2013.01); *G10L 21/0208* (2013.01); *H04R 1/10* (2013.01); *H04R 1/1016* (2013.01); *H04R 29/004* (2013.01)

(56) References Cited

U.S. PATENT DOCUMENTS

| | | | | |
|---|---|---|---|---|
| 4,890,619 | A * | 1/1990 | Hatschek | A61B 5/14552 600/323 |
| 4,991,587 | A * | 2/1991 | Blakeley | A61B 5/0456 128/901 |
| 5,549,652 | A * | 8/1996 | McClure | A61N 1/3712 607/28 |
| 5,832,093 | A * | 11/1998 | Bernstein | A61B 7/04 381/67 |
| 8,200,339 | B2 | 6/2012 | Wiskerke | H04R 1/08 607/36 |
| 8,340,309 | B2 * | 12/2012 | Burnett | G10K 11/1784 381/71.6 |
| 8,545,417 | B2 * | 10/2013 | Banet | A61B 5/0402 600/529 |
| 2002/0143242 | A1 * | 10/2002 | Nemirovski | H04B 1/3877 600/300 |
| 2003/0220584 | A1 * | 11/2003 | Honeyager | A61B 5/02125 600/559 |
| 2004/0249633 | A1 * | 12/2004 | Asseily | H04R 1/342 704/200 |
| 2005/0119586 | A1 * | 6/2005 | Coyle | A61B 5/0806 600/538 |
| 2005/0240087 | A1 * | 10/2005 | Keenan | A61B 5/0205 600/301 |
| 2006/0140425 | A1 * | 6/2006 | Berg | A61B 5/00 381/312 |
| 2006/0241510 | A1 * | 10/2006 | Halperin | A61B 5/113 600/534 |
| 2007/0014423 | A1 * | 1/2007 | Darbut | H04R 25/65 381/330 |
| 2008/0027341 | A1 * | 1/2008 | Sackner | A61B 5/0205 600/509 |
| 2009/0105548 | A1 * | 4/2009 | Bart | A61B 5/02438 600/300 |
| 2009/0281435 | A1 * | 11/2009 | Ahmed | A61B 5/02416 600/502 |
| 2010/0016745 | A1 * | 1/2010 | Crump | A61B 5/02055 600/519 |
| 2010/0113948 | A1 * | 5/2010 | Yang | A61B 5/02416 600/500 |
| 2010/0125218 | A1 * | 5/2010 | Haartsen | A61B 5/02438 600/528 |
| 2010/0160795 | A1 * | 6/2010 | Banet | A61B 5/02125 600/485 |
| 2010/0189268 | A1 * | 7/2010 | Haartsen | A61B 5/6817 381/56 |
| 2010/0217102 | A1 * | 8/2010 | LeBoeuf | A61B 5/00 600/310 |
| 2011/0066041 | A1 * | 3/2011 | Pandia | A61B 5/113 600/484 |
| 2011/0319703 | A1 * | 12/2011 | Wiskerke | H04R 25/30 600/25 |
| 2012/0197093 | A1 * | 8/2012 | LeBoeuf | A61B 5/7207 600/301 |
| 2014/0051939 | A1 * | 2/2014 | Messerschmidt | A61B 5/0205 600/301 |
| 2014/0128753 | A1 * | 5/2014 | Luna | A61B 5/02438 600/500 |
| 2014/0128754 | A1 * | 5/2014 | Luna | A61B 5/746 600/500 |
| 2014/0276227 | A1 * | 9/2014 | Perez | A61B 5/4818 600/586 |
| 2014/0288447 | A1 * | 9/2014 | Luna | A61B 5/02438 600/508 |
| 2014/0303521 | A1 * | 10/2014 | Nakamura | A61B 7/04 600/586 |
| 2015/0018636 | A1 * | 1/2015 | Romesburg | A61B 5/721 600/301 |
| 2015/0141774 | A1 * | 5/2015 | Ogawa | A61C 17/22 600/301 |

* cited by examiner

HEART RATE DETECTION METHOD USED IN EARPHONE AND EARPHONE CAPABLE OF DETECTING HEART RATE

TECHNICAL FIELD

The invention relates to the field of earphone and heart rate detection technology, particularly to a heart rate detection method used in an earphone and an earphone capable of detecting heart rate.

DESCRIPTION OF RELATED ART

With the continuous development of social economy, people's material standard of living improves with each passing day, and people are paying more attention to their health. Heart rate detection will provide very important information on health for people. Any display of abnormal heart rate will indicate a problem of health, thus heart rate detection can find out whether or not our body has a problem without delay. Heart rate detection can also reflect to some extent whether or not human's motion intensity is appropriate. In order to achieve the optimum effect of exercise, people should keep their heart rate within a certain scope in the course of exercise, and the heart rate detection can provide an index for a reasonable amount of exercise.

In addition, lots of people like wearing an earphone to listen to music during exercise. In order to detect the heart rate during exercise without the need to carry around other devices, people start to study relevant technology of how to detect heart rate by using an earphone.

For heart rate detection technology, in addition to heart rate belt, a technology of detecting heart rate by using an earphone emerges at present to achieve the purpose of convenience and accuracy.

The technology of detecting heart rate by using an earphone just emerged in recent years. On Oct. 23 to 25, 2013, Kaiteki Corporation and Bifrostec Corporation exhibited a technology of detecting pulse fluctuation by using an earphone at a health-equipment exhibition in Yokohama, Japan. The technology uses the earphone clinging to the auditory meatus to form an enclosed space, and a certain pressure will be generated in the auditory meatus because of vibration of the eardrum, and the pressure will change with the change of vibration. Information of the pressure change in the auditory meatus will be collected by a microphone, thus the purpose of detecting heart rate can be achieved. However, the earphone cannot occupy the entire auditory meatus, which will cause a leak of the air in the auditory meatus, and, as a result, the microphone cannot detect the change of the pressure and the heart rate detection will be interfered by external noises.

BRIEF SUMMARY OF THE INVENTION

In view of aforesaid problem, the present invention provides a heart rate detection method used in an earphone and an earphone capable of detecting heart rate to overcome aforesaid problem or at least partly solve aforesaid problem.

The present invention provides a heart rate detection method used in an earphone, wherein the method comprises:

providing a cavity inside the earphone, and installing a microphone in the cavity; the position where an opening of said cavity clings to a shell of the earphone is the position where the shell of the earphone clings to an auricle of a wearer when the earphone is worn; the shell of the earphone is provided with a hole at the position where the opening of said cavity clings to, and when the earphone is worn, the cavity and the auricle which the hole clings to form an enclosed space;

collecting signals generated by pressure change in said cavity by said microphone when the earphone is worn;

taking the signals collected by the microphone as signals related to heart rate; and detecting heart rate according to the signals related to heart rate.

Optionally, the method comprises: providing an acceleration sensor in the earphone;

collecting signals generated by body movement of the wearer by the acceleration sensor when the earphone is worn;

performing self-adaptive filtering process on the signals collected by the acceleration sensor to obtaining estimated signals of the signals generated by body movement of the wearer in the signals collected by the microphone;

subtracting the estimated signals from the signals collected by the microphone to obtain signals related to heart rate.

The present invention also provides an earphone capable of detecting heart rate, wherein the earphone comprises: a heart rate detection unit, a cavity provided in the earphone, and a microphone installed in the cavity;

wherein the position where an opening of the cavity clings to a shell of the earphone is the position where the shell of the earphone clings to an auricle of a wearer when the earphone is worn; the shell of the earphone is provided with a hole at the position where the opening of the cavity clings to, and when the earphone is worn, the cavity and the auricle which the hole clings to form an enclosed space;

the microphone is configured to collect signals generated by pressure change in the cavity when the earphone is worn, the signals collected by the microphone are being taken as signals related to heart rate; and the heart rate detection unit is configured to detect heart rate according to the signals related to heart rate.

Optionally, the earphone further comprises: an acceleration sensor, a self-adaptive filtering unit, and a subtractor;

the acceleration sensor is configured to collect signals generated by body movement of the wearer and output the signals to the self-adaptive filtering unit when the earphone is worn;

the self-adaptive filtering unit is configured to perform self-adaptive filtering process on the signals collected by the acceleration sensor according to the signals related to heart rate to obtaining estimated signals of the signals generated by body movement of the wearer in the signals collected by the microphone, output the estimated signals to the subtractor; and the subtractor is configured to subtract the estimated signals from the signals collected by the microphone to obtain the signals related to heart rate, and output the signals related to heart rate to the heart rate detection unit and the self-adaptive filtering unit.

As can be seen from the foregoing, the technical scheme in the embodiment of the invention uses the enclosed cavity formed by the cavity in the earphone and the earphone shell to place the microphone, which reduces interference of external noises, and reinforces signal information collected by the microphone. The acceleration sensor is further added to the earphone for collecting signals generated due to human body movement, and the influence of the human body movement on heart rate detection is eliminated by designing the self-adaptive filter.

Above description is only a summary of the technical scheme of the present invention. In order to know the technical means of the present invention more clearly so that it can be put into effect according to the content of the description, and to make the aforesaid and other purpose, features and advantages of the invention clearer, the embodiments of the invention will be described in further detail with reference to the drawings.

DETAILED DESCRIPTION OF THE INVENTION

The embodiments of the present disclosure are described in further detail with reference to the drawings below. Although the drawings show the embodiments of the present disclosure, it should be understood that the disclosure can be implemented in various forms and is not intended to be limited by the embodiments described here. On the contrary, the embodiments are provided to make the invention understood more thoroughly and completely convey the scope of the disclosure to a person skilled in the art.

Figure 1:
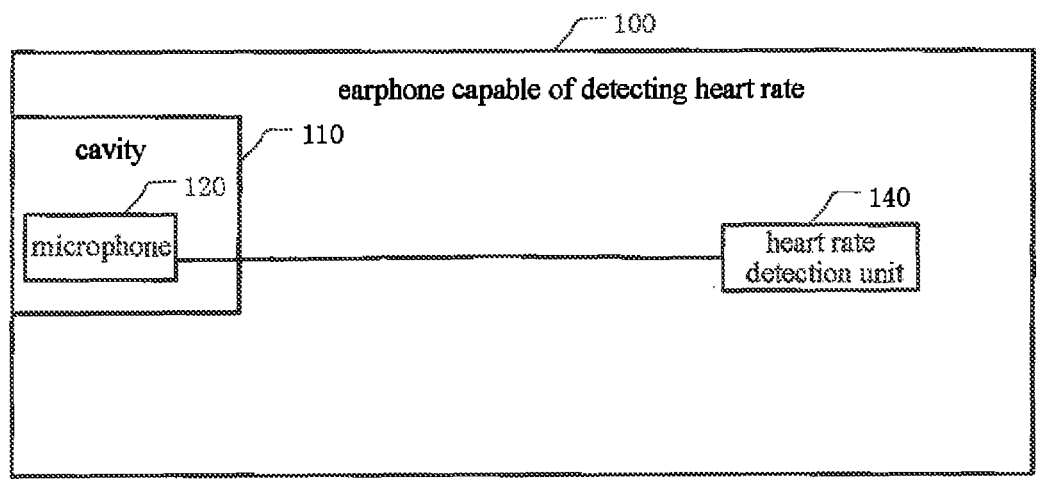
FIG. 1 is a structural diagram of an earphone capable of detecting heart rate in an embodiment of the present invention.

FIG. 1 is a structural diagram of an earphone capable of detecting heart rate in the embodiment of the present invention. As shown in FIG. 1, the earphone 100 capable of detecting heart rate comprises: a heart rate detection unit 140, a cavity 110 provided in the earphone, and a microphone 120 installed in the cavity 110;

Wherein the position where an opening of the cavity 110 clings to a shell of the earphone is the position where the shell of the earphone clings to an auricle of a wearer when the earphone is worn; the shell of the earphone is provided with a hole at the position where the opening of the cavity 110 clings to, and when the earphone is worn, the cavity and the auricle which the hole clings to form an enclosed space;

the microphone 120 is configured to collect signals generated by pressure change in the cavity 110 when the earphone is worn;

the heart rate detection unit 140 is configured to detect heart rate according to the signals collected by the microphone 120.

In the earphone 100 capable of detecting heart rate shown in FIG. 1, the small cavity 110 is provided in the earphone 100 to place the microphone 120 and forms an enclosed space with the auricle, which reduces interference of external noises, and reinforces signal information collected by the microphone 120.

In an embodiment of the invention, the heart rate detection unit 140 is configured to detect the cycle of the signals which are collected by the microphone and have been filtered, and obtain heart rate from the reciprocal of the detected cycle of the signals.

In prior arts of detecting heart rate by an earphone, an microphone is generally directly placed in the earphone at a position just directed at the auditory meatus, for collecting pressure change information in the ear cavity generated by vibration of the eardrum. But on one hand, since the space formed by the earphone and the auditory meatus is large, a leak of the air in the auditory meatus will be caused, thus the pressure change information collected by the microphone is very weak; on the other hand, generally the earphone cannot occupy the entire auditory meatus, thus there will be interference from external noises if the microphone is directly placed in the earphone. Therefore, for the earphone shown in FIG. 1 of the invention, another way to install the microphone is designed; see FIG. 2A-2C for specifics.

Figure 2A:
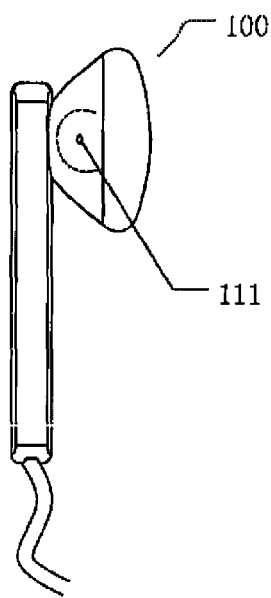
FIG. 2A is a lateral schematic diagram of the earphone 100 provided with a cavity 110 in the embodiment of the present invention.
Figure 2B:
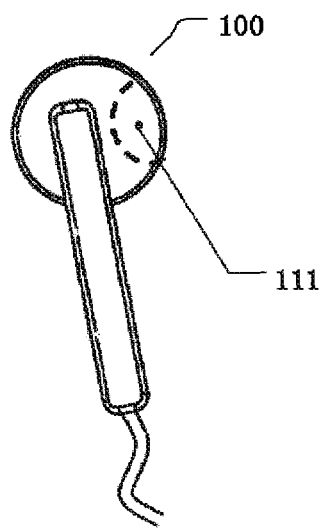
FIG. 2B is a back schematic diagram of the earphone 100 provided with the cavity 110 in the embodiment of the present invention.
Figure 2C:
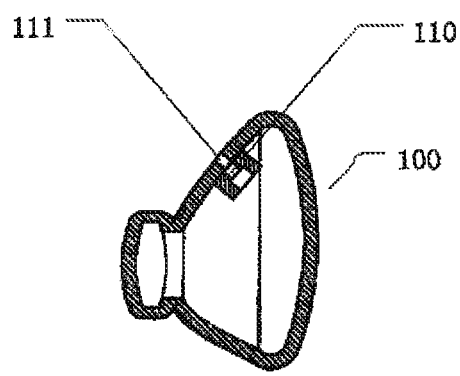
FIG. 2C is a lateral section view of the earphone 100 provided with the cavity 110 in the embodiment of the present invention.

FIG. 2A is a lateral schematic diagram of an earphone 100 provided with a cavity 110 in the embodiment of the present invention. FIG. 2B is a back schematic diagram of an earphone 100 provided with a cavity 110 in the embodiment of the present invention. FIG. 2C is a lateral section view of an earphone 100 provided with a cavity 110 in the embodiment of the present invention. In order to better collect useful signals related to heartbeat, the present invention designs a small cavity for placing the microphone. See FIG. 2A and FIG. 2B, the scope in the dashed line shown in the figures shows the position of the cavity 110 formed inside the earphone. See FIG. 2C, an opening of the cavity 110 clings to the earphone shell. As can be seen, in the embodiment, the cavity 110 is at the edge of the earphone at a position close to the auricle, and the earphone is provided with a hole 111 at the position where the cavity clings to. When the earphone is worn, the hole 111 is tightly attached to the auricle, thus the cavity 110 and the part of the auricle that presses close to the cavity form an enclosed space. The microphone is installed in the cavity 110, and shrink and vibration of the auricle wall will cause change of the pressure in the cavity 110, thus the microphone will collect the pressure change information in the cavity 110. The information reflects the frequency of heartbeats to some extent, thus heart rate can be detected hereby.

In physics, for an enclosed space (without regard to temperature), intensity of pressure is inversely proportional to volume. That is to say, the smaller the volume, the larger the intensity of pressure, and the larger the pressure acting on a certain area. When a user wears the earphone, an enclosed space is formed in the auditory meatus, and the fluctuation of pulse pressure of the vessel will cause shrink of the ear wall, thus certain pressure change will be generated in the cavity. The pressure change signal will be detected by the microphone. Generally speaking, the fluctuation of pulse pressure of the vessel is very weak. The larger the enclosed space, the smaller the pressure change that can be detected by the microphone. In order to enhance the intensity of the pressure change detected by the microphone, the embodiment installs the microphone in an enclosed small cavity and the small cavity closely clings to the auditory meatus. Since the fluctuation of pulse pressure of the vessel causes shrink and vibration of the ear wall, the vibration makes the microphone in the small cavity detect change of the pressure. And the design of the small cavity will reduce the influence of external interference signals.

Figure 3:
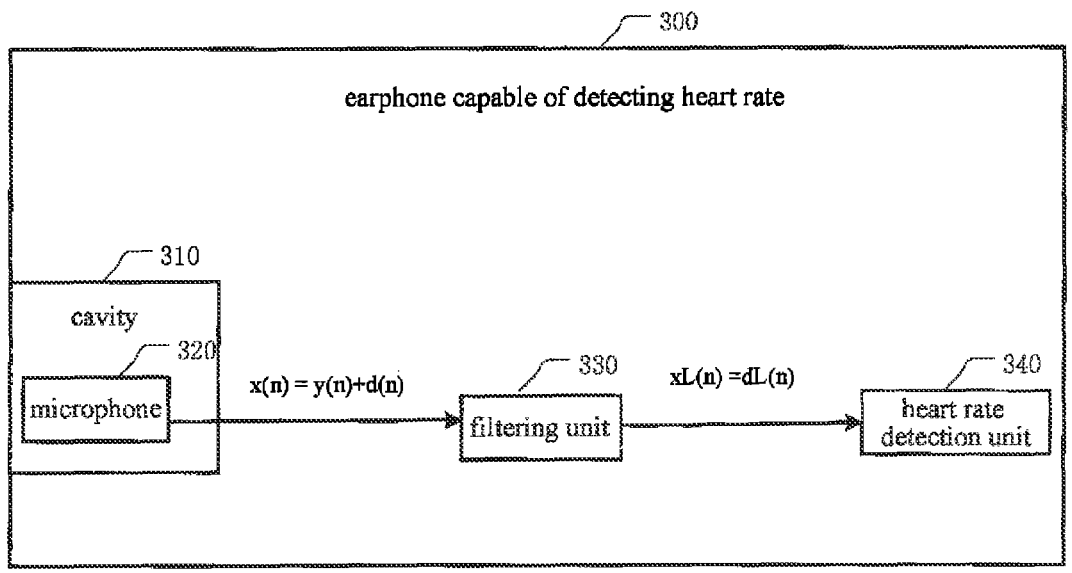
FIG. 3 is a structural diagram of an earphone capable of detecting heart rate in another embodiment of the present invention.

FIG. 3 is a structural diagram of an earphone capable of detecting heart rate in another embodiment of the present invention. As shown in FIG. 3, the earphone 300 capable of detecting heart rate comprises: a filtering unit 330, a heart rate detection unit 340, a cavity 310 provided in the earphone, and a microphone 320 installed in the cavity 310;

Wherein the position where an opening of the cavity 310 clings to a shell of the earphone is the position where the shell of the earphone clings to an auricle of a wearer when the earphone is worn; the earphone shell is provided with a hole at the position where the opening of the cavity 310 clings to, and when the earphone is worn, the cavity and the auricle where the hole clings to form an enclosed space;

the microphone 320 is configured to collect signals generated by pressure change in the cavity 310 when the earphone is worn, and output the corresponding signals to the filtering unit 130;

the filtering unit 330 is configured to perform filtering process on the signals collected by the microphone 320 to obtain the filtered signals and output the signals to the heart rate detection unit 340. Here the filtering unit filters the signals collected by the microphone 320 to eliminate the influence of the interference noise on heart rate detection.

The heart rate detection unit 340 is configure to detect heart rate according to the filtered signals.

In an embodiment of the invention, the heart rate detection unit 340 is configured to detect the cycle of the signals related to heart rate, and obtain heart rate from the reciprocal of the detected cycle of the signals. For example, the heart rate detection unit 340 can detect the cycle of the signals related to heart rate by using autocorrelation method and threshold value method, etc.

In an embodiment of the invention, the filtering unit 330 shown in FIG. 3 comprises: a low pass filter configured to perform low pass filtering process on signals collected by the microphone 320 to filter out high-frequency interference signals. This is because that the frequency of pulse vibration is relatively low (0.3 Hz-3 Hz or so) while the frequency of external noise is higher. According to this feature, the influence of external high-frequency noise can be eliminated via the low pass filter. For example, the low pass filter can be an FIR filter of which cut-off frequency is 5 Hz.

In the earphone shown in FIG. 3, the low pass filter is adopted to perform low pass filtering process on signals collected by the microphone. As shown in FIG. 3, the microphone in a small cavity is used first for collecting pressure signals in the cavity; then the low pass filter is used for performing low pass filtering on the signals collected by the microphone; at last, after the heart rate signal is obtained, heart rate can be detected. Heartbeat has certain periodicity, thus heart rate signal is a signal with certain periodicity. The cycle corresponding to the signal can be obtained according to autocorrelation method, and the reciprocal of the cycle is heart rate.

The specific process is as follows:
Suppose the signal detected by the microphone is: $x(n)=y(n)+d(n)$;

wherein $y(n)$ represents interference signal; $d(n)$ represents the pressure change signal generated by flow of blood; and n represents sampling time point;

After low pass filtering, the signal of $x(n)$ becomes: $xL(n)=dL(n)$. The external noise signal collected by the microphone will be filtered out after low pass filtering.

After $dL(n)$ is obtained, according to periodicity characteristic of the signal, the cycle can be detected by using autocorrelation method, threshold value method, etc, and the reciprocal of the cycle is heart rate.

Via the earphone in the embodiment shown in FIG. 1 or FIG. 3, heart rate of human under various conditions (still, moving, etc) can be obtained, so that information of physical condition of human body can be obtained, or on this basis human can control their amount of exercise within an appropriate scope in accordance with specific conditions.

On the basis of aforesaid embodiment, a heart rate detection method used in an earphone of the present invention is provided.

Figure 4:
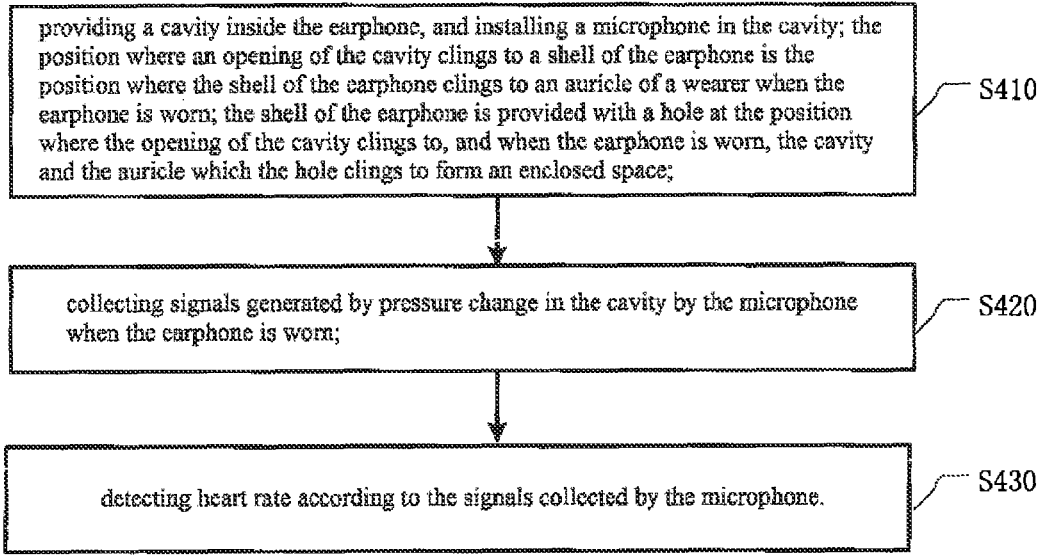
FIG. 4 is a flowchart showing a heart rate detection method used in an earphone in an embodiment of the present invention.

FIG. 4 is a flowchart showing a heart rate detection method used in an earphone in the embodiment of the present invention. As shown in FIG. 4, the method comprises:

Step S410, providing a cavity inside the earphone, and installing a microphone in the cavity; the position where an opening of the cavity clings to a shell of the earphone is the position where the shell of the earphone clings to an auricle of a wearer when the earphone is worn; the shell of the earphone is provided with a hole at the position where the opening of the cavity clings to, and when the earphone is worn, the cavity and the auricle which the hole clings to form an enclosed space;

Step S420, collecting signals generated by pressure change in the cavity by the microphone when the earphone is worn;

Step S430, detecting heart rate according to the signals collected by the microphone, that is, taking the signals collected by the microphone as signals related to heart rate, and detecting the heart rate according to the signals related to heart rate.

In an embodiment of the invention, before Step S430, the method shown in FIG. 4 further comprises: performing filtering process on the signals collected by the microphone to obtain the filtered signals. Detecting heart rate according to the signals collected by the microphone in Step S430 comprises: detecting heart rate according to the filtered signals.

In an embodiment of the invention, performing filtering process on the signals collected by the microphone of the method shown in FIG. 4 comprises: performing low pass filtering process on the signals collected by the microphone to filter out high-frequency interference signal.

In an embodiment of the invention, detecting heart rate according to the filtered signals comprises: detecting the cycle of the filtered signals, and obtaining heart rate from the reciprocal of the detected cycle of the signals.

In summary, the beneficial effect of the technical scheme of aforesaid embodiment of the present invention comprises that: (1) the enclosed cavity with a relatively small volume is used for placing the microphone, which reduces interference of external noises, and reinforces signal information detected by the microphone. (2) According to feature of the frequency of pulse vibration, a low pass filter is designed to further reduce the influence of external high-frequency noise.

For using an earphone to detect heart rate, there is another important factor affecting accurate detection of heart rate, that is, human body movement. Human body movements will inevitably cause vibration of ear wall, and this vibration similarly will cause pressure change in auditory meatus. This pressure change will be collected by the microphone, thus interferes the analysis on heart rate signals. Thus, the invention provides the following solution.

Figure 5:
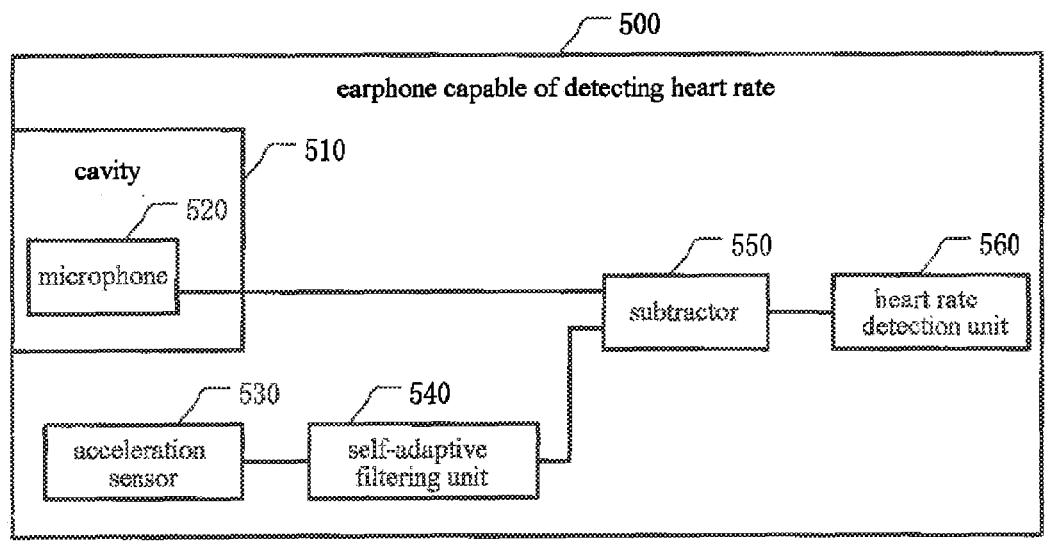
FIG. 5 is a structural diagram of an earphone capable of detecting heart rate in an embodiment of the present invention.

FIG. 5 is a structural diagram of an earphone capable of detecting heart rate in the embodiment of the present invention. As shown in FIG. 5, the earphone 500 capable of detecting heart rate comprises: a subtractor 550, a heart rate detection unit 560, an acceleration sensor 530, a self-adaptive filtering unit 540, a cavity 510 provided in the earphone, and a microphone 520 installed in the cavity 510; wherein the position where an opening of the cavity 510 clings to a shell of the earphone is the position where the earphone shell clings to the auricle of human ears when the earphone is worn; the earphone shell is provided with a hole at a position where the opening of the cavity 510 clings to, and when the earphone is worn, the cavity and the auricle which the hole clings to form an enclosed space.

The microphone 520 is configured to collect signals generated by pressure change in the cavity 510 and output the signals to the subtractor 550 when the earphone 500 is worn.

The acceleration sensor 530 is configured to collect signals generated by body movement of a wearer and output the signals to the self-adaptive filtering unit 540 when the earphone is worn.

The self-adaptive filtering unit 540 is configured to perform self-adaptive filtering process on the signals collected by the acceleration sensor 530 according to signals related to heart rate, and after obtaining estimated signals of the signals generated by body movement of the wearer in the signals collected by the microphone 520, output the estimated signals to the subtractor 550.

The subtractor 550 is configured to subtract the estimated signals outputted by the self-adaptive filtering unit 540 from the signals collected by the microphone to obtain signals related to heart rate and output the signals to the heart rate detection unit 560 and the self-adaptive filtering unit 540.

The heart rate detection unit 560 is configured to detect heart rate according to the signals related to heart rate.

Self-adaptive filtering process is performed on the signals detected by the acceleration sensor 530 in FIG. 5, so that human motion signal collected by the microphone 520 can be accurately estimated from human motion signal collected by the acceleration sensor 530, and the purpose is to eliminate the influence of human body movement on heart rate detection. The microphone 520 and the acceleration sensor 530 both will detect the vibration signal generated by human body movement. Cycles of the two kinds of signals are the same, but amplitudes are different, thus a self-adaptive filter is needed to be used for eliminating this difference, so that the acceleration signal generated by body movement can be eliminated from the signals collected by the microphone to obtain effective heart rate information.

In the earphone 500 capable of detecting heart rate shown in FIG. 5, the cavity 510 is arranged in the earphone 500 for placing the microphone 520, which reduces interference of external noises, and reinforces signal information collected by the microphone 520. In addition, the earphone 500 capable of detecting heart rate comprises the acceleration sensor 530 to collect signals generated by body movement of the wearer, and performs self-adaptive filtering on the signals collected by the acceleration sensor 530, and subtracts the acceleration sensor signals after self-adaptive filtering from the signals collected by the microphone, and then detects heart rate. Thereby the influence of body movement of the wearer on the heart rate detection is eliminated.

In an embodiment of the invention, the earphone shown in FIG. 5 further comprises a low pass filter, for performing low pass filtering process on the signals collected by the microphone, obtaining the low pass filtered signals and outputting the signals to the subtractor 550. That is, the subtractor 550 is configured to subtract the estimated signals outputted by the self-adaptive filtering unit 540 from the low pass filtered signals to obtain signals related to heart rate and output the signals to the heart rate detection unit. This is because that the frequency of pulse vibration is relatively low (0.3 Hz-3 Hz or so) while the frequency of external noise is higher. According to this feature, the influence of external high-frequency noise can be eliminated via the low pass filter. For example, the low pass filter can be an FIR filter of which the cut-off frequency is 5 Hz.

The specific way of providing the cavity 510 in the earphone 500 and installing the microphone 520 in the cavity 510 in the present embodiment are same with the scheme shown in FIGS. 2A-2C, thus it will not be repeated here.

Figure 6:
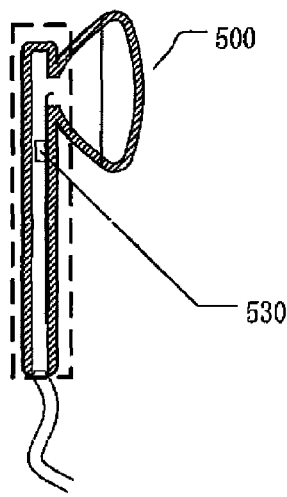
FIG. 6 is a diagram showing the installing position of an acceleration sensor in an embodiment of the present invention.

FIG. 6 is a diagram showing the installing position of an acceleration sensor in an embodiment of the present invention. Movement of human body will cause vibration of human skin accompanying with it, thus the acceleration sensor in the embodiment is installed in the earphone at a position not contacting the skin, so as to avoid the influence of vibration of the skin on the signals collected by the acceleration sensor and increase the accuracy of the signals collected by the acceleration sensor. See FIG. 6, the acceleration sensor 530 can be installed at any position of the earphone 500 shown by the dashed box in FIG. 6.

In practice, even if the earphone can occupy the entire auditory meatus to form a completely enclosed cavity, the influence of human body movement on heart rate detection is inevitable, because human body movement will inevitably cause vibration of the ear wall, and pressure change in the cavity generated by the vibration will similarly be detected by the microphone. Thus the data collected by the microphone comprises not only the pressure change information generated by the fluctuation of pulse pressure of the vessel, but also the pressure change information generated in auditory meatus by human body movement. In order to eliminate the influence of the human body movement on heart rate detection, the present invention adds the acceleration sensor in the earphone, and the acceleration sensor is installed in the earphone at a position not contacting the skin, for example, the position of the earphone shown by the dashed box in FIG. 6. The acceleration sensor is used for collecting acceleration information generated by human body movement. The pressure change information generated in auditory meatus by human body movement has same vibration frequency with acceleration information, and on this basis a certain filter can be adopted to eliminate the interference generated by human body movement.

According to the foregoing analysis, if the signals generated due to human body movement can be eliminated from the signals detected by the microphone, then the signals generated by the shrink of the auditory meatus per se caused by flow of blood can be obtained. The signals are relevant to the frequency of heartbeat, and heart rate information can be obtained based on the signals.

The microphone collects the pressure change information in auditory meatus caused by human body movement, and the acceleration sensor collects acceleration information corresponding to the human body movement. Though the two kinds of signals have same vibration frequencies, i.e. same cycles, their amplitudes are different. The signals cannot be directly taken out from the signals collected by the microphone, thus the embodiment filters out the interference generated due to human body movement in the method of self-adaptive filtering.

In summary, in the embodiment of the invention: first, the enclosed cavity with a relatively small volume is used for placing the microphone, which reduces interference of external noises, and reinforces signal information detected by the microphone. Second, the acceleration sensor is added to the earphone for collecting signals generated by human body movement, and the self-adaptive filter is designed to further eliminate the influence of the human body movement on heart rate detection. Furthermore, according to the feature of the frequency of pulse vibration, a low pass filter is designed to further reduce the influence of external noises. It will be further described below with FIG. 7 as an example.

Figure 7:
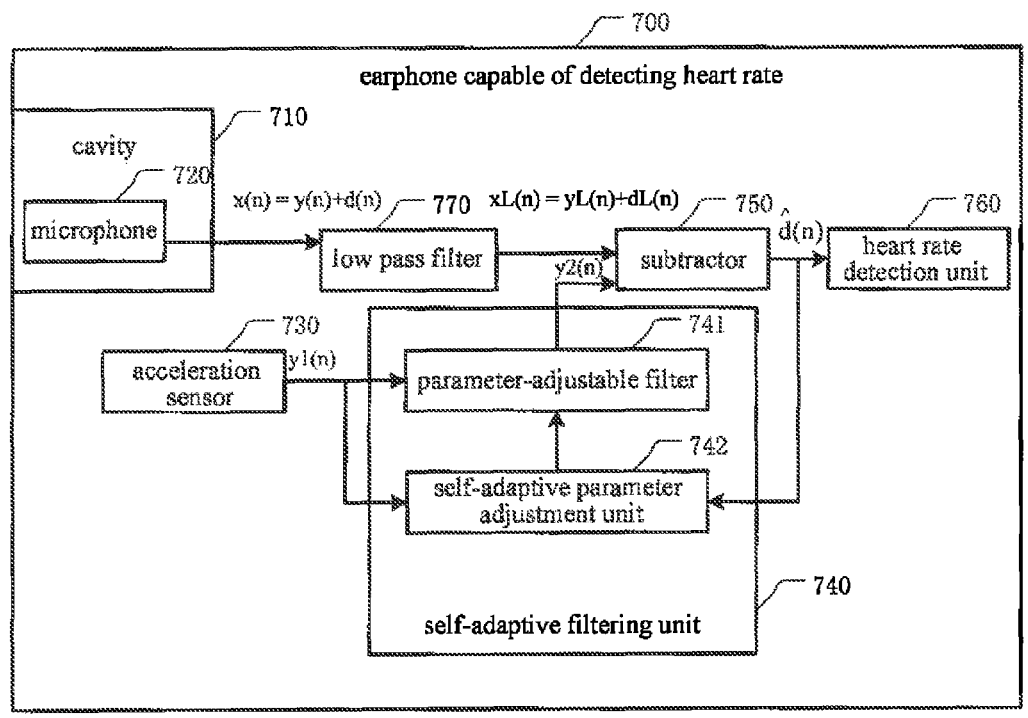
FIG. 7 is a structural diagram of an earphone capable of detecting heart rate in another embodiment of the present invention.

FIG. 7 is a structural diagram of an earphone capable of detecting heart rate in another embodiment of the present invention. As shown in FIG. 7, the earphone 700 capable of detecting heart rate comprises: a subtractor 750, a heart rate detection unit 760, a low pass filter 770, an acceleration sensor 730, a self-adaptive filtering unit 740, a cavity 710 provided in the earphone and a microphone 720 installed in the cavity 710. Wherein, the self-adaptive filtering unit 740 comprises: a parameter-adjustable filter 741 and a self-adaptive parameter adjustment unit 742.

Wherein the position where an opening of the cavity 710 clings to a shell of the earphone is the position where the shell of the earphone clings to the auricle of a wearer when the earphone is worn; the earphone shell is provided with a hole at a position where the opening of the cavity 710 clings to, and when the earphone is worn, the cavity and the auricle which the hole clings to form an enclosed space.

The microphone 720 is configured to collect signals generated by pressure change in the cavity 710 and output the signals to the low pass filter 770 when the earphone 700 is worn.

The low pass filter 770 is configured to perform low pass filtering process on signals collected by the microphone 720 and output the low pass filtered signals to the subtractor 750.

The acceleration sensor 730 is configured to collect signals generated by body movement of the wearer when the earphone is worn and output the signals to the parameter-adjustable filter 741 and the self-adaptive parameter adjustment unit 742 in the self-adaptive filtering unit 740.

The self-adaptive parameter adjustment unit 742 is configured to adjust filtering parameters of the parameter-adjustable filter 741 according to the signals collected by the acceleration sensor 730, the signals related to heart rate, and the preset self-adaptive algorithms.

The parameter-adjustable filter 741 is configured to perform self-adaptive filtering on the signals collected by the acceleration sensor 730 by using the filtering parameters, and output the estimated signals of the signals generated by body movement of the wearer in the signals collected by the microphone 720 to the subtractor 750.

The subtractor 750 is configured to subtract the estimated signals outputted by the parameter-adjustable filter 741 from the signals outputted by the low pass filter to obtain signals related to heart rate, and output the signals to the heart rate detection unit 760; the subtractor 750 is further configured to output the signals related to heart rate to the self-adaptive parameter adjustment unit 742.

Here the self-adaptive parameter adjustment unit 742 calculates the filtering parameters of the parameter-adjustable filter 741 by using self-adaptive algorithms according to the inputted signals collected by the acceleration sensor 730 and the signals related to heart rate fed back by the subtractor 750.

The heart rate detection unit 760 is configured to detect heart rate according to the signals related to heart rate.

In an embodiment of the invention, the heart rate detection unit 760 is configured to detect the cycle of the signals related to heart rate, and obtain heart rate from the reciprocal of the detected cycle of the signals. For example, the heart rate detection unit 760 can detect the cycle of the signals related to heart rate by using existing autocorrelation method and threshold value method, etc.

Figure 8:
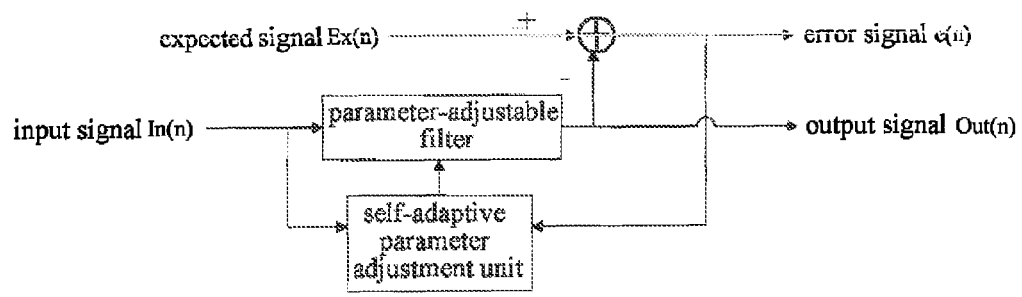
FIG. 8 is a general structural diagram of a self-adaptive filter.

FIG. 8 is a general structural diagram of a self-adaptive filter. As shown in FIG. 8, the self-adaptive filter mainly consists of a parameter-adjustable filter and a self-adaptive parameter adjustment unit for adjusting coefficient of the filter. The self-adaptive filter does not need to know the knowledge of statistical property of the relevant signals in advance when it is designed. It can gradually "know" or estimate the required statistical property in the course of work and automatically adjust its own parameters according to this, so as to achieve the optimum filtering effect. In FIG. 8, Ex(n) is expected signal; In(n) is input signal; Out(n) is output signal; e(n) is evaluated error; and e(n)=Ex(n)−Out(n). The filtering coefficient of the self-adaptive filter is controlled by the error signal, and e(n) adjusts the self-adaptive coefficient by presetting self-adaptive algorithms, so as to make the mean square error of e(n) the smallest eventually. Now the output signal is most approximate to the expected signal.

In the earphone shown in FIG. 7, the self-adaptive filter is adopted to perform filtering process on the signals collected by the acceleration sensor to accurately estimate the signals generated due to human body movement collected by the microphone. As shown in FIG. 7, $y1(n)$ is the signal collected by the acceleration sensor 730, i.e. corresponding to the input signal in the self-adaptive filtering unit 740, and $y2(n)$ is the output signal of the self-adaptive filtering unit 740. xL(n) represents the corresponding desired signal, and $\hat{d}(n)$ is corresponding to the error signal (mainly comprising heart rate signal). There is certain correlation between yL(n) and $y1(n)$, thus the output signal $y2(n)$ of $y1(n)$ after the filter can become approximate to yL(n) by designing an appropriate transfer function. For example, according to the minimum mean square error principle, when the expected value of mean square of the error signal is minimum, the output signal $y2(n)$ can be used for effectively estimating yL(n), and then the interference of human body movement on heart rate detection can be eliminated from the signals collected by the microphone, then further eliminating the influence of interference signals. The signals of the microphone after low pass filtering subtracts the signals of the acceleration sensor after self-adaptive filtering, obtaining signal information $\hat{d}(n)$ related to heart rate, and on this basis heart rate can be detected. The beat of heart has certain periodicity, thus $\hat{d}(n)$ is the signal with certain periodicity. The cycle corresponding to the signal can be obtained according to autocorrelation method, and the reciprocal of the cycle is heart rate.

The specific process is as follows:

suppose the signals detected by the microphone is: x(n)=y(n)+d(n); and the signals detected by the acceleration sensor is y1(n).

Wherein y(n) represents pressure change signal generated due to human body movement; d(n) represents pressure change signal generated by the flow of blood; y1(n) represents acceleration signal generated due to human body movement and n represents sampling time point.

After low pass filtering, the signal of x(n) becomes: xL(n)=yL(n)+dL(n).

y1(n) and y(n) are both signals generated by the same movement. y1(n) is corresponding to acceleration information, and y(n) is corresponding to pressure information. Although amplitudes corresponding to the two are different, their vibration frequencies are the same. In order to eliminate y(n) from x(n), a self-adaptive filter (impact response is h(n)) is selected to filter y1(n), obtaining y2(n)=y1(n)*h(n), so that y2(n) can be as approximate as possible to pressure change signal yL(n) generated due to human body movement in x(n) after low pass filtering.

Thus the signals generated because of shrink of the auditory meatus can be expressed as:

$$\hat{d}(n)=xL(n)-y2(n).$$

The self-adaptive parameters of the filter is obtained by using self-adaptive algorithms. There are many methods of realizing the self-adaptive algorithms. For example, the method of minimum mean square error can be adopted, that is, obtaining coefficient of the filter when the value of $E(\hat{d}^2(n))$ is minimum.

After $\hat{d}(n)$ is obtained, according to the periodicity characteristic of the signal, the cycle can be detected by using autocorrelation method, threshold value method, etc, and the reciprocal of the cycle is heart rate.

Via the earphone in the embodiment shown in FIG. 5 or FIG. 7, people's heart rate under various conditions (still, moving, etc) can be obtained, so that the information of physical condition of human body can be obtained, or on this basis people can control their amount of exercise within an appropriate scope in accordance with specific conditions.

On the basis of aforesaid embodiment, the heart rate detection method used in an earphone of the present invention is provided. For the specific content of each step in the embodiment of the method of the invention, see the description related to the embodiment of the product of the invention.

Figure 9:
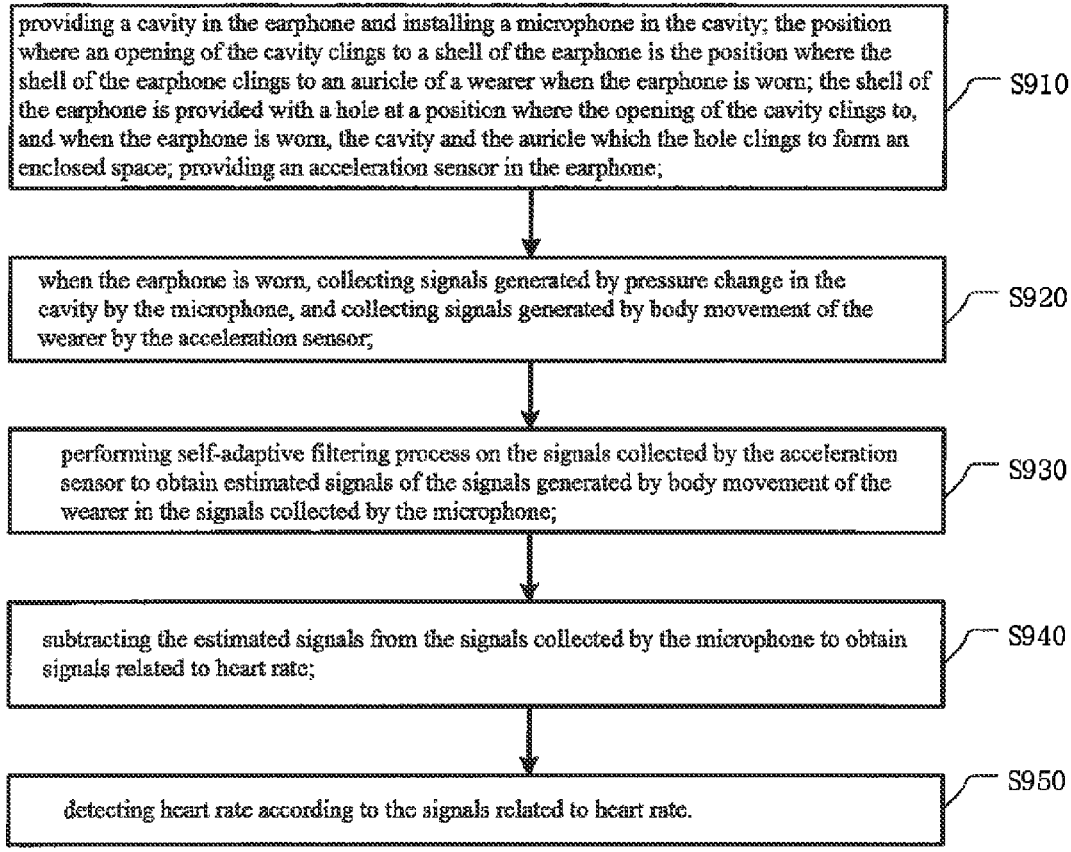
FIG. 9 is a flowchart showing a heart rate detection method used in an earphone in the embodiment of the present invention.

FIG. 9 is a flowchart showing a heart rate detection method used in an earphone in the embodiment of the present invention. As is shown in FIG. 9, the method comprises:

Step S910, providing a cavity in the earphone and installing a microphone in the cavity; the position where an opening of the cavity clings to a shell of the earphone is the position where the shell of the earphone clings to an auricle of a wearer when the earphone is worn; the shell of the earphone is provided with a hole at a position where the opening of the cavity clings to, and when the earphone is worn, the cavity and the auricle which the hole clings to form an enclosed space; providing an acceleration sensor in the earphone. For example, the acceleration sensor can be provided in the earphone at a position not contacting the skin of a wearer;

Step S920, when the earphone is worn, collecting signals generated by pressure change in the cavity by the microphone, and collecting signals generated by body movement of the wearer by the acceleration sensor;

Step S930, performing self-adaptive filtering process on the signals collected by the acceleration sensor to obtain estimated signals of the signals generated by body movement of the wearer in the signals collected by the microphone;

Step S940, subtracting the estimated signals from the signals collected by the microphone to obtain signals related to heart rate;

Step S950, detecting heart rate according to the signals related to heart rate.

In an embodiment of the invention, before subtracting the estimated signals from the signals collected by the microphone to obtain the signals related to heart rate, the method shown in FIG. 9 further comprises: performing low pass filtering process on the signals collected by the microphone to obtain low pass filtered signals. Then the subtracting the estimated signals from the signals collected by the microphone to obtain the signals related to heart rate in Step S940 specifically comprises: subtracting the estimated signals from the low pass filtered signals to obtain the signals related to heart rate.

In an embodiment of the invention, performing self-adaptive filtering process on the signals collected by the acceleration sensor to obtain estimated signals of the signals generated by body movement of the wearer in the signals collected by the microphone in Step S930 comprises:

calculating self-adaptive filtering parameters according to the signals collected by the acceleration sensor, the signals related to heart rate and the preset self-adaptive algorithms;

performing self-adaptive filtering on the signals collected by the acceleration sensor according to the self-adaptive filtering parameters to obtain the estimated signal.

In an embodiment of the invention, detecting heart rate according to the signals related to heart rate in Step S950 comprises: detecting cycle of the signals related to heart rate, and obtaining the heart rate from the reciprocal of the detected cycle of the signals.

In summary, the beneficial effect of the technical scheme in the embodiment shown in FIGS. 5-9 of the present invention comprises:

(1) The enclosed cavity with a relatively small volume is used for placing the microphone, which reduces interference of external noises, and reinforces signal information detected by the microphone.

(2) The acceleration sensor is added to the earphone for collecting signals generated due to human body movement, and the self-adaptive filter is designed to eliminate the influence of human body movement on heart rate detection.

(3) According to feature of the frequency of pulse vibration, a low pass filter is designed to further reduce the influence of external high-frequency noise.

The foregoing descriptions merely show preferred embodiments of the present invention, and are not intended to limit the protection scope of the present invention. Any modification, equivalent replacement and improvement made within the spirit and principle of the present invention shall fall into the protection scope of the present invention.

The invention claimed is:

1. A heart rate detection method used in an earphone, wherein said method comprises:
    providing a cavity inside the earphone, the cavity being defined by a shell of the earphone;
    installing a microphone in said cavity,
    positioning the shell of the earphone in communication with an auricle of a wearer when the earphone is worn;

providing a hole in the shell of the earphone, the hole being positioned in the shell such that when the earphone is worn, said cavity and the auricle form an enclosed space;

collecting signals generated by pressure change in said cavity by said microphone when the earphone is worn;

taking the signals collected by the microphone as signals related to heart rate; and detecting heart rate according to the signals related to heart rate.

2. The method according to claim 1, wherein the method further comprises:

performing filtering process on the signals collected by said microphone to obtain filtered signals;

said detecting heart rate according to the signals related to heart rate comprises: detecting heart rate according to said filtered signals.

3. The method according to claim 1, wherein said method comprises:

providing an acceleration sensor in the earphone;

collecting signals generated by body movement of the wearer by said acceleration sensor when the earphone is worn;

performing self-adaptive filtering process on the signals collected by said acceleration sensor to obtain estimated signals of the signals generated by body movement of the wearer in the signals collected by the microphone;

subtracting said estimated signals from the signals collected by the microphone to obtain signals related to heart rate.

4. The method according to claim 3, wherein before subtracting said estimated signals from the signals collected by the microphone to obtain signals related to heart rate, the method further comprises: performing low pass filtering process on the signals collected by said microphone to obtain low pass filtered signals;

said subtracting said estimated signals from the signals collected by the microphone to obtain signals related to heart rate specifically comprises: subtracting said estimated signals from said low pass filtered signals to obtain signals related to heart rate.

5. The method according to claim 3, wherein said performing self-adaptive filtering process on the signals collected by said acceleration sensor to obtain estimated signals of the signals generated by body movement of the wearer in the signals collected by the microphone comprises:

calculating self-adaptive filtering parameters according to the signals collected by the acceleration sensor, the signals related to heart rate and preset self-adaptive algorithms;

performing self-adaptive filtering on the signals collected by the acceleration sensor according to said self-adaptive filtering parameters to obtain said estimated signals.

6. The method according to claim 3, wherein said detecting heart rate according to the signals related to heart rate comprises:

detecting the cycle of said signals related to heart rate;

obtaining heart rate from reciprocal of the detected cycle of the signals.

7. The method according to claim 3, wherein said providing an acceleration sensor in the earphone comprises: installing the acceleration sensor in the earphone at a position not contacting the wearer's skin.

8. An earphone capable of detecting heart rate, wherein the earphone comprises:

a heart rate detection unit, a cavity provided in the earphone, and a microphone installed in said cavity;

wherein:

the cavity in the earphone is defined by a shell of the earphone;

the shell of the earphone is positionable in communication with an auricle of a wearer when the earphone is worn;

the shell of the earphone is provided with a hole being positioned in the shell such that when the earphone is worn, said cavity and the auricle form an enclosed space;

said microphone is configured to collect signals generated by pressure change in said cavity when the earphone is worn, the signals collected by the microphone being taken as signals related to heart rate; and said heart rate detection unit is configured to detect heart rate according to the signals related to heart rate.

9. The earphone according to claim 8, wherein the earphone further comprises:

a filtering unit configured to perform filtering process on signals collected by said microphone and output filtered signals to said heart rate detection unit.

10. The earphone according to claim 8, wherein the earphone also comprises: an acceleration sensor, a self-adaptive filtering unit, and a subtractor;

said acceleration sensor is configured to collect signals generated by body movement of the wearer and output the signals to said self-adaptive filtering unit when the earphone is worn;

said self-adaptive filtering unit is configured to perform self-adaptive filtering process on the signals collected by said acceleration sensor according to the signals related to heart rate to obtain estimated signals of the signals generated by body movement of the wearer in the signals collected by the microphone, and output the estimated signals to said subtractor; and said subtractor is configured to subtract said estimated signals from the signals collected by the microphone to obtain the signals related to heart rate, and output the signals related to heart rate to said heart rate detection unit and said self-adaptive filtering unit.

11. The earphone according to claim 10, wherein the earphone further comprises: a low pass filter configured to perform low pass filtering process on signals collected by said microphone, and output low pass filtered signals to said subtractor;

said subtractor is configured to subtract said estimated signals from said low pass filtered signals to obtain the signals related to heart rate, and outputting the signals related to heart rate to said heart rate detection unit.

12. The earphone according to claim 10, wherein said self-adaptive filtering unit comprises: a parameter-adjustable filter and a self-adaptive parameter adjustment unit;

said acceleration sensor is configured to output the collected signals to said parameter-adjustable filter and said self-adaptive parameter adjustment unit;

said subtractor is configured to output said signals related to heart rate to said self-adaptive parameter adjustment unit;

said self-adaptive parameter adjustment unit is configured to adjust filtering parameters of said parameter-adjustable filter according to the signals collected by the acceleration sensor, the signals related to heart rate, and preset self-adaptive algorithms; and said parameter-adjustable filter is configured to perform self-adaptive filtering on the signals collected by the acceleration sensor by using the filtering parameters, and output the estimated signals of the signals generated by body movement of the wearer in the signals collected by the microphone to said subtractor.

13. The earphone according to claim 10, wherein
said heart rate detection unit is configured to detect the cycle of said signals related to heart rate, and obtain heart rate from reciprocal of the detected cycle of the signals.

14. The earphone according to claim 10, wherein
said acceleration sensor is installed in the earphone at a position not contacting the wearer's skin.

\* \* \* \* \*